United States Patent [19]

Patel

[11] 4,276,190

[45] * Jun. 30, 1981

[54] PROCESS FOR MONITORING TIME-TEMPERATURE HISTORIES OF PERISHABLES UTILIZING INACTIVE FORM OF DIACETYLENE

[75] Inventor: Gordhanbhai N. Patel, Morris Plains, N.J.

[73] Assignee: Allied Chemical Corporation, Morris Township, Morris County, N.J.

[*] Notice: The portion of the term of this patent subsequent to Feb. 19, 1999, has been disclaimed.

[21] Appl. No.: 60,936

[22] Filed: Jul. 26, 1979

Related U.S. Application Data

[62] Division of Ser. No. 938,174, Aug. 30, 1978, Pat. No. 4,208,186.

[51] Int. Cl.³ .............................................. C09K 3/00
[52] U.S. Cl. .................................. 252/408; 252/600; 73/356; 116/202; 116/207; 250/474; 426/88; 204/159.19
[58] Field of Search ............... 252/408, 300, 600; 204/159.19; 426/88; 250/474; 73/356, 358; 23/230 R, 230 TD; 116/202, 206, 207; 430/56

[56] References Cited

U.S. PATENT DOCUMENTS

| | | | |
|---|---|---|---|
| 3,501,297 | 3/1970 | Cremeans | 430/374 |
| 3,723,121 | 3/1973 | Hauser | 430/374 |
| 3,981,683 | 9/1976 | Larssen | 116/207 |
| 3,999,946 | 12/1976 | Patel | 252/408 X |
| 4,042,336 | 8/1977 | Larssen | 23/253 TP |
| 4,189,399 | 2/1980 | Patel | 252/300 |

*Primary Examiner*—Benjamin R. Padgett
*Assistant Examiner*—J. L. Barr
*Attorney, Agent, or Firm*—Robert A. Harman; Alan M. Doernberg

[57] ABSTRACT

An improved process and device are described, for monitoring time-temperature histories of perishable articles, utilizing an inactive form of a diacetylene compound, incapable of undergoing a color change upon thermal annealing, but capable of conversion to an active form upon contacting an activating vapor. The active form is capable of undergoing a color change upon thermal annealing, as a result of solid state polymerization wherein the resulting color change is representative of the time-temperature history of thermal annealing. Specific active and inactive forms of diacetylenes useful in the improved process and device are also described.

2 Claims, 3 Drawing Figures

PROCESS FOR MONITORING TIME-TEMPERATURE HISTORIES OF PERISHABLES UTILIZING INACTIVE FORM OF DIACETYLENE

This is a division of application Ser. No. 938,174, filed Aug. 30, 1978 now U.S. Pat. No. 4,208,186.

BACKGROUND OF THE INVENTION

1. Field of the Invention

This invention relates to an improved process and device for monitoring time-temperature histories of perishable articles wherein an inactive form of a diacetylene compound, containing at least one —C≡C—C≡C group, is contacted with an activating vapor to convert it to an active form, capable of undergoing a color change upon thermal annealing.

2. Brief Description of the Prior Art

Time-temperature history indicators are known in the art which incorporate diacetylene compounds as the active indicator and are described in U.S. Pat. No. 3,999,946 (Patel et al. to Allied Chemical, 1976), the subject matter of which is hereby incorporated by reference.

U.S. Pat. No. 3,501,297 discloses a process for producing visual photographic images wherein a colorless mixture of diacetylenes is exposed to ultraviolet radiation, thereby being converted to a deep blue/bronze color, and then transforming the resulting mixture to a red product by exposing to warm ethanol vapors for about 5 minutes. However, such a process does not suggest a device in which an inactive form of diacetylene can be converted to an active form of diacetylene by contacting with a vapor.

U.S. Application Ser. No. 854,933 (Patel and Yee, to Allied Chemical, 1977), the subject matter of which is hereby incorporated by reference, discloses a device in which an inactive diacetylene is converted by melt or solvent recrystallization to an active form, capable of exhibiting a color response upon thermal annealing. However, the device requires contacting inactive diacetylene compound with liquid solvent for the activation process, said quantity of solvent representing an economically unattractive aspect of activating such devices.

The references Zeit. fur Naturforschung V. 24b, pp. 824–832 (1969) by G. Wegner, and Acta Cryst. (1978) B34, 143–147, by J. J. Mayerle and T. C. Clarke, disclose that the bis(p-chlorophenylurethane) of 2,4-hexadiyn-1,6-diol is relatively inactive toward photopolymerization and thermally induced polymerization.

U.S. Pat. No. 3,981,683 (1976) describes a sterility indicator comprising a backing strip of a dimensinally stable material, e.g. aluminum foil, having mounted thereon an organic compound, containing oxygen or nitrogen, in intimate contact with a wicking means and a cover strip bonded to the backing strip overlaying the organic compound and wicking means. The cover strip is a polymeric rate controlling film which permits water vapor to pass through at a rate sufficient to make the device operative at a temperature to be monitored. However, the use of inactive forms of diacetylenes as indicating materials is not suggested or mentioned.

U.S. Pat. No. 4,042,336 (1977) describes a device for measuring the time-temperature history of a product in which the history is displayed as a color front on an indicator, the distance of front advancement being a function of the temperature-time integral. However, the use of inactive forms of diacetylenes as indicating materials, which can be converted to active forms upon contacting an activating vapor, is not suggested or mentioned.

We have unexpectedly found that an inactive form of a diacetylene compound, containing at least one —C≡C—C≡C—group, can be activated prior to use, by allowing the inactive form to be contacted with a vapor, thus converting the inactive form to an active form, capable of undergoing a color change upon thermal annealing.

SUMMARY OF THE INVENTION

In accordance with this invention there is provided in a process for monitoring the time-temperature history of an article including the steps of: (a) applying to an article an integral time-temperature history indicator comprising a diacetylene compound, containing at least one —C≡C—C≡C—group, capable of undergoing a color change upon thermal annealing, after contacting an activating vapor, said color change being representative of the integrated time-temperature history of thermal annealing; and (b) providing said vapor to said diacetylene compound; the improvement which comprises providing said diacetylene compound in an inactive form, capable of being converted to an active form upon contacting said activating vapor, said active form capable of undergoing a color change upon thermal annealing.

Also, there is provided in a device for monitoring time temperature history of a perishable article including (a) a substrate having deposited thereon a diacetylene compound, containing at least one —C≡C—C≡C— group, capable of undergoing a color change upon thermal annealing, after contacting an activating vapor, said color change being representative of the integrated time-temperature history of thermal annealing, and (b) a source of said vapor, the improvement which comprises said diacetylene compound in an inactive form, capable of being converted to an active form upon contacting said vapor, said active form capable of undergoing a color change upon thermal annealing.

In addition there is provided an article having applied thereto the above-described improved device of this invention.

Also provided is a composition selected from the group consisting of the inactive forms of: 2,4-hexadiyn-1,6-diol bis(m-tolylurethane), 2,4-hexadiyn-1,6-diol bis-(o-methoxyphenylurethane), 2,4-hexadiyn-1,6-diol bis (o-chlorophenylurethane), mixtures and co-crystallized compositions thereof, capable of conversion to an active form which can undergo a color change upon thermal annealing.

Further provided is a composition selected from the group consisting of the active forms of 2,4-hexadiyn-1,6-diol bis(m-tolylurethane), 2,4-hexadiyn-1,6-diol bis-(o-methoxyphenylurethane), 2,4-hexadiyn-1,6-diol bis-(o-chlorophenylurethane), 2,4-hexadiyn-1,6-diol bis(p-chlorophenylurethane), and mixtures thereof, capable of undergoing a color change upon thermal annealing.

DESCRIPTION OF THE INVENTION AND PREFERRED EMBODIMENTS

Figure 3:
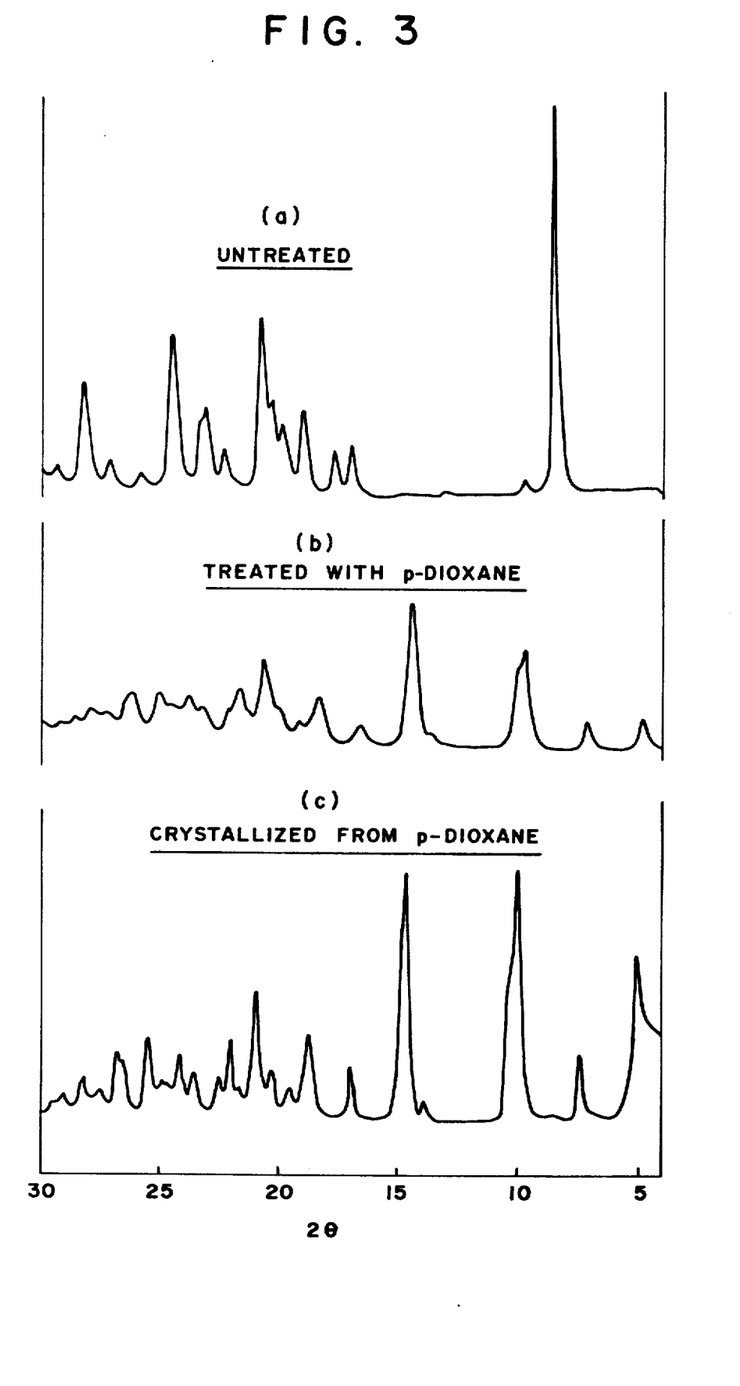
FIG. 3 illustrates X-ray diffraction patterns of 2,4-hexadiyn-1,6-diol bis(m-tolylurethane) HDDmTU: (a) the inactive form crystallized from acetone/hexane; (b) the inactive form in (a) treated with p-dioxane vapor resulting in the active form; and (c) the inactive form in (a) crystallized from p-dioxane resulting in the inactive form.

The novelty of this invention resides in the fact that certain diacetylene compositions exist in what is termed "active" and "inactive" forms. The term, "active form" as used herein, refers to those crystalline phases, mesomorphs or modifications of a solid diacetylenic composition which can undergo solid state polymerization via 1,4-addition reactions which can occur through conjugated diyne groups, i.e. —C≡C—C≡C—, in the monomeric molecule. The solid state polymerization can be induced by thermal annealing or at temperatures of at least about 0° C. and above. The term, "inactive form" as used herein, refers to those crystalline forms, mesomorphs or phases which do not undergo solid state polymerization upon thermal annealing but are capable of conversion to an active form upon contacting an activating vapor. The term "inactive form" as used herein is not intended to cover crude materials or crude reaction products, which are generally incapable of undergoing a conversion to the active form by contacting a vapor. The terms "inactive" and "active" form as used herein are not to be construed as being equivalent or identical to the terms used in U.S. Application Ser. No. 854,933, filed Nov. 25, 1977, in which the terms refer to different crystallographic forms, as distinguished by X-ray diffraction spectroscopy, in which the inactive form can be converted to an active form only by solvent or melt recrystallization. By contrast, the inactive form of diacetylene included in this invention process may be converted to the active form upon solvent or melt recrystallization, but irrespective of this, is capable of being converted to the active form specifically by contacting an activating vapor therefor, capable of converting the inactive to an active form. Also, the inactive and active forms may generally, but not necessarily, be distinguished on the basis of their X-ray diffraction patterns as illustrated in FIG. 3.

Diacetylene compositions, in general, can exist in both active and inactive forms, but only a select few, existing in an inactive form, can be substantially activated by contact with an activating vapor to be transformed into an active form, capable of undergoing solid state polymerization upon thermal annealing. The term "thermal annealing" as used herein, refers to heating at sufficient temperature, as by infrared radiation, flame, laser-beam, microwave radiation and the like which is sufficiently energetic to cause chemical changes, i.e. polymerization, by 1,4-addition of the active diacetylenic compound.

Compositions which can be prepared in an inactive form and then converted into an active form upon contacting an activating vapor include:

| Chemical Name | Abbreviation |
|---|---|
| 2,4-hexadiyn-1,6-diol bis (m-tolylurethane) | HDDmTU |

-continued

| Chemical Name | Abbreviation |
|---|---|
| 2,4-hexadiyn-1,6-diol bis (o-methoxyphenylurethane) | HDDoMPU |
| 2,4-hexadiyn-1,6-diol bis (o-chlorophenylurethane) | HDDoCPU |
| 2,4-hexadiyn-1,6-diol bis (p-chlorophenylurethane) | HDDpCPU |

One embodiment of this invention is a composition selected from the group consisting of the inactive forms of HDDmTU, HDDoMPU, HDDoCPU, mixtures and co-crystallized compositions thereof, capable of conversion to an active form which can undergo a color change upon thermal annealing. The conversion can be accomplished for example, by contacting the inactive form with an activating vapor selected from the group consisting of p-dioxane, dimethylformamide, pyridine, or mixtures thereof.

Also an embodiment of this invention is a composition selected from the group consisting of the active forms of HDDmTU, HDDoMPU, HDDoCUP, HDDpCPU, or mixtures thereof, capable of undergoing a color change upon thermal annealing.

The term "co-crystallized composition", as used herein, refers to a composition comprised of at least two diacetylene compounds, wherein the composition exhibits a substantially different thermogram than the sum of the thermograms of the individual components as obtained by differential scanning calorimetry. The term is adequately described in U.S. Application Ser. No. 817,069, filed July 19, 1977 by G. N. Patel now U.S. Pat. No. 4,189,399 (Allied Chemical being the assignee). However, the above reference does not describe co-crystallized compositions, in the inactive form, capable of being converted by contacting a vapor to the active form, which undergoes a color change upon thermal annealing.

Examples of co-crystallized compositions in the instant invention process include a 90/10 weight percent composition of 2,4-hexadiyn-1,6-diol bis(phenylurethane), HDDPU, and 2,4-hexadiyn-1,6-diol bis(p-chlorophenylurethane), HDDpCPU. This composition can be prepared by rapidly precipitating a tetrahydrofuran solution of the two diacetylenes, in the stated weight percentages, by mixing the solution with cold hexane at −70° C. Since HDDPU, in an inactive form, is not capable of being converted to the active form by contacting an activating vapor, co-crystallization with HDDpCPU provides a means for preparing a suitable inactive compound useful in the invention process.

Other diacetylenic compositions which also possess this property are equivalents and are included in the scope of the invention.

General methods of preparing compounds having the above molecular formula are adequately described in U.S. Pat. No. 3,999,946 (Patel et al. to Allied Chemical (1976)), which is hereby incorporated by reference.

Methods of preparing the inactive form of diacetylene compounds useful in this invention process include: (a) dissolving a mixture of two or more diacetylenes in a solvent therefor, and rapidly removing the solvent from the reaction to quickly precipitate the dissolved solid; (b) dissolving a mixture of two or more diacetylenes in a solvent and causing the dissolved solid the precipitate by the addition of a second solvent, miscible with the original solvent, but acting as a non-solvent for the solid; and (c) recrystallizing a mixture of two or more diacetylenes from a solvent or solvent mixture via either slow or rapid crystal growth.

For example, HDDmTU can be prepared in the inactive form by dissolving in chloroform, dichloromethane, nitromethane, acetone/hexane (60:40 by volume) and spraying the solution onto a suitable surface such as filter paper to rapidly deposit the solid and to evaporate the solvent. The resulting solid is in the inactive form, ready for use in a time-temperature history indicator. Similarly, inactive forms of HDDoMPU, HDDpCPU, HDDoCPU, or mixtures thereof, can also be prepared.

Also, the inactive form of HDDmTU, can be prepared by method (b), described above, wherein, crude HDDmTU is dissolved in acetone and a sufficient amount of hexane, a non-solvent for the solid, added to quickly precipitate the diacetylene in the inactive form.

Similarly, the inactive form of HDDmTU can be prepared by recrystallizing from acetone/hexane (60:40 by volume) and slowly allowing the crystals to form.

Physical differences between the inactive and active forms are generally evident in their respective X-ray crystallographic spectra, as illustrated in FIG. 3 for HDDmTU. The inactive form is unreactive to polymerization upon thermal annealing or exposure to ultraviolet and gamma-radiation as produced for example from conventional sources such as an ultraviolet lamp and Co 60 isotope. The inactive form is also unreactive toward polymerization upon thermal annealing by, for example, heating said inactive form below its respective melting point for several hours. In general, the inactive forms are colorless, whereas the active forms are colored in various degrees of red or blue.

Activating vapors capable of converting inactive diacetylenic compositions to the active form include p-dioxane, dimethylformamide, pyridine, or mixtures thereof. The amount of activating vapor necessary to effect a conversion is an amount necessary to contact said inactive composition on the surface of the inactive form and is usually less than about 50 weight percent of said inactive form. Upon contacting an inactive form with a vapor, the change to an active form occurs almost simultaneously.

The improved invention process can be conducted by utilizing the improved invention device embodying the compositions of the invention and suitable vapors, capable of converting the inactive form of the diacetylene composition to active form.

In general, the device comprises an indicator including an inactive form of diacetylene compound, containing at least one conjugated diyne group, i.e. —C≡C—C≡C—, capable of being converted to an active form upon contacting an activating vapor. The active form is then capable of undergoing a color change upon thermal annealing in which the color change is representative of the integrated time-temperature history of thermal annealing. A suitable device is constructed such that substantially all of the inactive form, at least on the outer surface of the indicator, is converted to the active form upon contact with said vapor.

Figure 1:
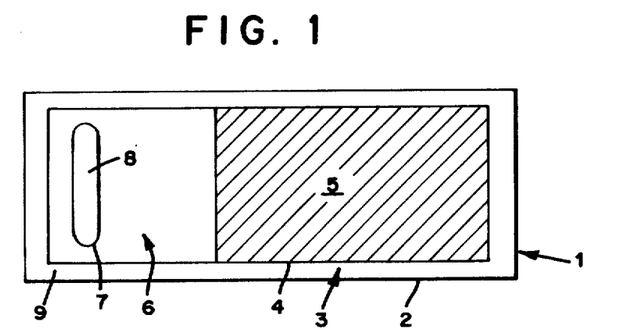
FIG. 1 is an illustration of the top view of a device suitable in a preferred embodiment of the invention process showing closed container 2, indicator 3 and means 6 for providing vapor.
Figure 2:
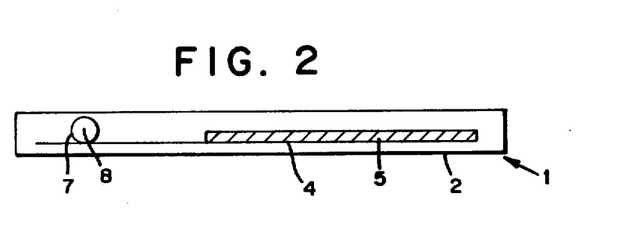
FIG. 2 is an illustration of a side view of the above device described and illustrated in FIG. 1.

A preferred embodiment of the invention device can be readily described by reference to FIG. 1 and FIG. 2. As is seen in FIG. 1, device 1 includes a closed container 2 in which is housed indicator 3 and means 6 for providing vapor. Indicator 3 is comprised of a substrate 4 having inactive form diacetylene compound 5 deposited thereon. Means 6 for producing vapor is comprised of solvent 8 contained in frangible solvent capsule 7 positioned on absorptive substrate 9.

Device operation occurs when frangible solvent capsule 7 is ruptured, allowing solvent to escape and be absorbed by absorptive substrate 9. Evaporation of solvent from substrate 9 produces vapor which diffuses into closed container 2 and quickly saturates the inner atmosphere of the container. Upon contact of the inactive form of diacetylenic compound 5 of the indicator with the vapor, said compound undergoes a conversion from an inactive form to an active form and upon thermal annealing, i.e. exposure to a thermal environment to initiate solid-state polymerization, a color change in the compound is produced. A visual color response, such as a color change from white to blue or red, occurs over the entire exposed surface of the indicator substantially simultaneously. The produced color intensifies with time and temperature.

Knowledge of the time required, from the start of the monitoring period taken as the moment solvent is released to the container, to reach the end of the monitoring period, taken as the substantially simultaneous color response of the entire exposed surface area, reveals the integrated temperature during the monitoring period.

Knowledge of the integrated temperature of the monitoring period will determine the elapsed time required for development of the entire color response. A particular indicating solid/vapor system will possess a characteristic induction period which will be known and used in a particular situation.

The improved device of this invention can be used for monitoring the time-temperature histories of perishable products over a temperature range of about $-70°$ to $+150°$ C. and from times ranging from about one minute to 2 years, depending on the choice of vapor and indicator, which will be obvious to one skilled in the art from the disclosure herein.

The characteristic "induction period" for a particular vapor/indicator system, such that the time required for color response to occur, after release of vapor to the system, can be predictably controlled as a function of temperature, choice of vapor and diacetylene composition. The term "induction period" as herein used, refers to the threshold time required for the indicator to evidence a noticable visual color response following release of vapor to the system.

The container of the device is a closed vaporimpermeable structure housing the vapor and indicator of the device. The container being closed, operates to contain and prevent any vapor from escaping out of the device and also to provide an observable view of the indicator during the monitoring period. Representative examples of suitable materials for constructing the container include polyesters, such as polyethylene terephthalate, polyamides, such as nylon-66 and polyacrylonitrile. A preferred material is nylon-66.

The size and design of the container can be varied to suit the particular article to be monitored. A limitation on the size of the device is that it must be large enough to exhibit an observable color response under the conditions of monitoring.

The indicator of the device must be capable of undergoing a conversion to active form upon contacting an activating vapor, and must be positioned in the device such that direct contact with liquid solvent is avoided. After contact with said vapor, said active form of the indicator undergoes a color response, preferably a color change, over its entire exposed surface substantially simultaneously, such that the color response is essentially uniform and no localized moving colored boundaries are present. The reason as to why the inactive form of diacetylene undergoes a conversion from inactive to active form upon contacting with an activating vapor is not clearly understood and may be due to a variety of mechanisms such as partial dissolution of a portion of the diacetylene by the vapor, a change in the crystallinity of the diacetylene, a change in the crystal structure of the diacetylene, formation of a vapor-solid complex, or the like. Regardless of the mechanism underlying the color response, the incorporation of a vapor-indicator combination into the device system is not specifically directed or predicated upon one particular mechanism, but is based generally upon the observed fact that a diacetylene in inactive form is capable of undergoing a conversion to active form upon contact with a vapor.

The indicator comprises an inactive form of diacetylene deposited on a substrate. The substrate can be any solid material which acts as a support for the solid during the monitoring process and in the simplest embodiment can be the inner surface of the container material. It is preferred, however, to use a separate flexible support such as filter paper. The indicating solid can be deposited on the substrate by means of contacting or spraying the substrate with a solution of the indicating solid and allowing the solvent to evaporate or alternately, dispersing the indicating solid in a suitable binder medium such as shellac, varnish, lacquer, vinyl, epoxy, or acrylic, known materials in the art, and then applied to the substrate.

Included among solids useful in the instant invention are those solids existing in an inactive form, not capable of undergoing a color response upon thermal annealing, but capable of undergoing conversion to an active form upon contacting with a vapor, said active form being capable of undergoing a color response upon thermal annealing. It will be obvious to one skilled in the art from this disclosure as to how to test for inactive forms capable of being converted to active forms upon contact with a suitable vapor. Examples of such solids include diacetylenes, such as HDDmTU, and HDDpCPU, HDDoCPU and HDDoMPU described above.

A preferred class of indicating solids are diacetylene compounds, or mixtures or co-crystallized compositions thereof, wherein said compound contains at least one conjugated diyne group, i.e. —C≡C—C≡C—, per molecule, being in an "inactive" form and capable of being converted to an "active" form by contact with an activating vapor. The compositions are adequately described hereinabove.

Activating vapor useful in the invention process are described hereinabove and include those which are capable of converting inactive forms of diacetylene compositions to the corresponding active forms upon contact. Representative examples of suitable activating vapor are selected from the group consisting of p-dioxane, dimethylformamide, pyridine, or mixtures thereof.

Means for providing activating vapor to the container at the beginning of the monitoring process is positioned on the other side of closed container from the indicator and is usually a frangible solvent reservoir. The reservoir being frangible, is easily ruptured, as for example, by hand pressure, at the beginning of the monitoring period. The solvent is allowed to vaporize to form vapor, usually by wetting an absorptive substrate, e.g., a porous substrate, such as filter paper, which allows the evaporation process and thus supply of vapor to the system to occur readily. The solvent reservoir can be constructed of a variety of materials with the proviso that the material is not soluble in the solvent. In one embodiment, the material is sufficiently non-permeable to the solvent such that escape of solvent to the container does not occur prior to the desired monitoring period, as illustrated in FIG. 1. Representative materials that can serve as the solvent reservoir include thin-walled glass, and frangible but vapor-impermeable plastics. A preferred material is thin-walled glass.

Indicator substrate 4 and absorptive substrate 9 usually are constructed of the same materials although they could be different depending upon the specific circumstances. The purpose of substrate 9 is to provide an absorbent surface from which vapor is easily formed in the container. The purpose of support 8 is to support the solvent reservoir and/or the indicating tab, and to provide a background to make easier visual observation of the color response, and to provide a surface from which vapor can easily be formed. Representative examples of materials include filter paper, cotton and absorptive tissue. Preferred material is filter paper.

A preferred embodiment of the improved device useful in the invention process is that illustrated in FIG. 1 wherein the indicator is comprised of HDDmTU as indicating solid; the container is constructed of polyester, preferably polyethylene terephthalate, and wherein the activating vapor is p-dioxane, dimethylformamide, pyridine, or mixtures thereof.

The improved invention process for monitoring the timetemperature history of an article comprises applying to the article an improved device, described herein, and providing vapor to contact the indicator at the beginning of the monitoring period. The device contains an attaching means, preferably an adhesive backing, by which it can be readily attached to an article to be monitored. Means for providing vapor to the device are discussed hereinabove and can be a frangible solvent reservoir, as described herein, which can easily be activated by hand pressure, for example. The monitoring process can be conducted at a temperature of about −70° to +150° C.; at atmospheric pressures and even reduced pressures in partial vacuum.

Also a part of the instant invention is an article having a device, as described herein, attached thereto, in which the article can be any perishable product, e.g. packaged vaccine, blood or frozen food.

The nature of the container, indicator, vapor and means for providing vapor to the device are fully and adequately described hereinabove. The indicator can be prepared by contacting the indicator substrate with a solution of the indicating solid and allowing the solvent to evaporate. Alternatively, the indicating solid may be dispersed in a medium such as a binder and applied to the substrate. The indicating tab can then be sealed in a material such as a polymer, by means of a sealer, such as a hot press sealer, glues and pressure-sensitive adhesives. Preferred is a hot press sealer. The other components of the device including the solvent reservoir 7 (containing solvent) absorptive supports 8 and 9 are also sealed in the container by means of the sealer to form the completed device.

The following examples are illustrative of the best mode of carrying out the invention, as contemplated by us, but should not be construed to be limitations on the scope or spirit of the instant invention. Parts by weight where given unless otherwise indicated.

EXAMPLE 1

Synthesis of 2,4-Hexadiyn-1,6-diol bis(m-tolylurethane), HDDmTU

A 500 ml 3-necked round bottom flask was fitted with a magnetic stirrer, an addition funnel and a thermometer. To the flask was added 11.0 grams (0.1 mole) of 2,4-hexadiyn-1,6-diol in 300 ml of THF, 0.5 g of di-t-butyltin-di-2-ethoxyhexanoate and 2 ml. of triethylamine. The resultant solution was stirred and 39.9 g (0.3 mole) of n-tolyl isocyanate was added dropwise over a period of half an hour. The reaction temperature was maintained at about 25° C. by a cold water bath. The reaction was allowed to proceed for 2 hours. Into the resultant solution about 1500 ml of hexane was poured. The precipitate was collected and dried under vacuum. The yield of the crude material was quantitative. Elemental and infrared analysis was conducted on a sample recrystallized from acetone-hexane, which was in the inactive form. The m.p. was 133° C. Analytical: Calculated for C,H,N,O: 70.21; 5.32; 7.45; 17.02. Found for C,H,N,O: 70.17; 5.20; 7.12; 17.21. Infrared spectrum (KBr Pellet):

Urethane group: 3320 cm$^{-1}$ (NH), 1718 and 1735 cm$^{-1}$. (COO), 1552 cm$^{-1}$ (NH, CN), 1250 cm$^{-1}$ (CN, NH). Aromatic C—H, meta-substituted, 792 and 715 cm$^{-1}$. Aromatic C≡C stretching 1005, and 1489 cm$^{-1}$.

EXAMPLES 2-4

Syntheses of

2. HDDoMPU, 2,4 hexadiyn-1,6-diol bis(o-methoxyphenylurethane);
3. HDDpCPU, 2,4-hexadiyn-1,6-diol bis(p-chlorophenylurethane);
4. HDDoCPU, 2,4-hexadiyn-1,6-diol bis(o-chlorophenylurethane);

Utilizing the general procedure of Example 1, the above three diacetylenes were prepared, from 2,4-hexadiyn-1,6-diol and the appropriate isocyanates listed below in Table I. The melting point of the pure monomers, recrystallized from acetone-hexane, are also listed in the Table. The structures of the monomers were confirmed by elemental and infrared analysis of samples recrystallized from acetone/hexane, and were obtained in inactive forms.

TABLE I

| Diacetylene | Diyndiol | Isocyanate | m.p. (°C.) |
|---|---|---|---|
| 2. HDDoMPU | 2,4-hexadiyn-1,6 diol | o-methoxyphenyl isocyanate | 130 ± 2 |
| 3. HDDpCPU | 2,4-hexadiyn-1,6 diol | p-chlorophenyl isocyanate | 214 ± 2 |
| 4. HDDoCPU | 2,4-hexadiyn-1,6 diol | o-chlorophenyl isocyanate | 127 ± 2 |

EXAMPLE 5

Preparation and Activation of Inactive Form of HDDmTU

One gram of HDDmTU was dissolved in 10 ml. of the following solvents:

(1) Acetone: Hexane (60:40 by volume)
(2) Chloroform
(3) Dichloromethane
(4) Nitromethane The solutions were sprayed onto filter paper (Whatman No. 1) and the solvent on each paper was volatilized by directing a stream of dry nitrogen gas over it. An inactive form of HDDmTU was obtained in each case. The inactive form in each case did not polymerize upon thermal annealing, as evidenced by the fact that the obtained inactive form remained colorless after several months exposure to room temperature.

The above obtained inactive forms were individually tested by placing them in a desiccator containing saturated p-dioxane vapor versus a non-sprayed crystal control. Time required for a resulting color change to occur, in each case from colorless to light blue, was taken as the induction period; i.e. the time required for conversion of the inactive phase to the active phase. The results are shown below in Table II.

TABLE II

| Solvent Used for Crystallization | Time Required to Turn Light Blue |
|---|---|
| (1) Chloroform | 130 ± 20 seconds |
| (2) Dichloromethane | About 3 minutes |
| (3) Nitromethane | About 3 minutes |
| (4) Acetone: hexane (60:40) | About 3 minutes |
| (5) Crystals | 45-55 minutes |

The above results indicate that slightly different reactivities of formed inactive phase of HDDmTU can be obtained by varying the solvent used for deposition.

In addition, the results indicate that p-dioxane vapor can transform the inactive form of HDDmTU into an active form which starts polymerizing under the conditions of thermal annealing, resulting in a blue color.

EXAMPLE 6

Selectivity of Vapor For The Activation Process

Five ml. of the following solvents listed below in Table III were placed, into 50 ml. glass vessels, respectively. Tissue paper was placed at the bottom of the jars to aid in rapid formation of vapor. A small beaker containing about 20 mg of inactive phase of HDDmTU was placed into the vessel, such that direct contact did not occur between the liquid and solid and the vessel was closed. (Inactive form of HDDmTU was obtained by recrystallizing crude HDDmTU from acetone/hexane). Table III shows the effect on the inactive form of HDDmTU after 96 hrs. of exposure to the different vapors.

TABLE III

| Vapor | Effect |
|---|---|
| 1. Carbon tetrachloride | no change |
| 2. 1,2-Dichloroethane | no change |
| 3. Dichloromethane | no change |
| 4. Chloroform | no change |
| 5. Ethyl acetate | no change |
| 6. Methyl acetate | no change |
| 7. Nitromethane | no change |
| 8. Methyl formate | no change |
| 9. Ethyl formate | no change |
| 10. Benzene | no change |
| 11. Toluene | no change |
| 12. Xylene | no change |
| 13. Cyclohexane | no change |
| 14. Petroleum ether | no change |
| 15. Hexane | no change |
| 16. Chlorobenzene | no change |
| 17. Carbon disulfide | no change |
| 18. Methanol | no change |
| 19. Diethyl ether | no change |
| 20. Dimethylacetamide | becomes dissolved |
| 21. Dimethylformamide | becomes dissolved |

TABLE III-continued

| Vapor | Effect |
| --- | --- |
| 22. Acetone | becomes dissolved |
| 23. 1,2-Dimethoxyethane | becomes dissolved |
| 24. p-Dioxane | blue color developed after about 30 minutes |
| 25. Pyridine | blue color developed after about 30 minutes |

As is seen from the above Table, a narrow selectivity exists in the choice of vapor for activating the inactive form of HDDmTU.

EXAMPLE 7

Selectivity of Diacetylene-Vapor Pairs

The following listed diacetylenes, in the inactive form:

| | Chemical Name | |
| --- | --- | --- |
| 1. | 2,4-Hexadiyn-1,6-diol | bis(m-methoxyphenylurethane) |
| 2. | 2,4-Hexadiyn-1,6-diol | bis(2-chloroethylurethane) |
| 3. | 2,4-Hexadiyn-1,6-diol | bis(phenylurethane) |
| 4. | 2,4-Hexadiyn-1,6-diol | bis(ethylurethane) |
| 5. | 2,4-Hexadiyn-1,6-diol | bis(2,5-dichlorophenylurethane) |
| 6. | 3,5-Octadiyn-1,8-diol | bis(p-chlorophenylurethane) |
| 7. | 3,5-Octadiyn-1,8-diol | bis(phenylurethane) |
| 8. | 3,5-Octadiyn-1,8-diol | bis(o-methoxyphenylurethane) |
| 9. | 3,5-Octadiyn-1,8-diol | bis(p-bromophenylurethane) |
| 10. | 4,6-Decadiyn-1,10-diol | bis(2,5-dimethoxyphenylurethane) |
| 11. | 5,7-Dodecadiyn-1,12-diol | bis(p-bromophenylurethane) | were prepared according to the general procedure as described in Example 1, using the appropriate diols and isocyanates and tested as described in Example 6 with each of the following vapors: acetone, benzene, carbon tetrachloride, chloroform, dichloromethane, p-dioxane, dimethylformamide, ethyl acetate, methanol, pyridine, tetrahydrofuran and toluene. None of the diacetylene monomers, listed above, exhibited conversion to the active form under the conditions. However, four other diacetylenes, HDDmTU, HDDoMPU, HDDpCPU and HDDoCPU were capable of undergoing conversion to the active form under the conditions used.

EXAMPLE 8

Convertibility of HDDoMPU

Crystals of inactive HDDoMPU (obtained by recrystallizing crude material from acetone/hexane) were exposed to p-dioxane vapor inside a closed vessel. A color change upon exposure to the p-dioxane vapor developed as a function of time and the results are summarized below in Table IV.

TABLE IV

| Time (hrs) | Observed Color |
| --- | --- |
| 0 | white |
| 1.3 | light pink |
| 2.0 | light pink |
| 3.6 | pink |
| 5.6 | pinkish violet |

However, contacting inactive form of HDDoMPU with the other 11 solvents listed in Example 6 did not convert the inactive phase to the active phase.

EXAMPLE 9

The crystalline inactive phase of HDDpCPU, (obtained by recrystallizing crude material from tetrahydrofuran/hexane) was exposed to dimethylformamide vapor inside a closed vessel by the general technique described in Example 8. A color change developed with time and results are summarized below in Table V.

TABLE V

| Time (hrs) | Observed Color |
| --- | --- |
| 0 | white |
| 4 | light bluish violet |
| 5 | blue violet |
| 8 | blue violet |

However, contacting inactive phase of HDDpCUP with the other 11 solvents described in Example 7 did not convert the inactive phase to the active phase.

EXAMPLE 10

Convertibility of HDDoCPU

The inactive form of HDDoCPU (obtained by recrystallization from acetone/hexane) was exposed to p-dioxane vapor and after 48 hours, turned violet. Exposure to the other 11 solvents described in Example 7 did not convert the inactive form to the active form.

EXAMPLE 11

Use of Mixture of Vapors to Vary the Induction Period

The inactive form of HDDmTU was exposed to the following vapor mixtures, by the general procedure described in Example 6. A color change developed with time at room temperature for each of the 1:1 by weight vapor mixtures. The results are listed below in Table VI.

TABLE VI

| Time (hrs) | Vapor-Mixtures | | |
| --- | --- | --- | --- |
| | p-dioxane/THF[a] | P-dioxane/Ethylacetate | p-dioxane/DCM[b] |
| 0 | white | white | white |
| 0.3 | pink | white | white |
| 0.6 | pink | white | white |
| 0.9 | blue | white | white |
| 1.6 | dark blue | light blue | white |
| 16.0 | dark blue | dark blue | white |
| 26.0 | very dark blue | very dark blue | blue |

[a]Tetrahydrofuran
[b]Dichloromethane

As can be seen from the above Table, the induction period (i.e. time required for the inactive form of diacetylene to become activated and develop noticeable color change) can be varied by using a mixture of vapors.

EXAMPLE 12

Activation of an Inactive Form of Co-crystallized Diacetylene

HDDPU, 90%, and HDDpCPU, 10% by weight, respectively, were co-crystallized into an inactive form by rapidly precipitating the diacetylenes in the stated weight percentages from tetrahydrofuran solution by mixing with hexane at −70° C. The inactive form was separately exposed to p-dioxane and pyridine vapors by the procedures as described in Example 7. The following Table VII illustrates the rate of color change at room temperature for the two vapor systems.

TABLE VII

| Time (hrs) | Vapor p-Dioxane | Pyridine |
|---|---|---|
| 0 | white | white |
| 0.25 | white | white |
| 0.75 | Very light blue | Light reddish |
| 3.0 | Light Blue | Reddish violet |

As is seen, different developed colors can be obtained from the same co-crystallized composition by selecting different vapor systems.

EXAMPLE 13

Effect of Co-Crystallization On The Induction Period

HDDmTU and HDDoTU were co-crystallized in different proportions by selectively mixing 10% solutions of HDDoTU and HDDmTU in acetone in the following proportions:

| Diacetylene | Weight Percent in the Obtained Solids | | | | |
|---|---|---|---|---|---|
| HDDoTU | 100 | 80 | 50 | 30 | — |
| HDDmTU | — | 20 | 50 | 70 | 100 |

The resulting solutions were then poured dropwise into hexane under continuous stirring. The resultant co-crystallized precipitates were filtered and dried. A small quantity of the above described co-crystallized compositions was exposed to p-dioxane vapor in a closed vessel by the general procedure described in Example 7. A color change developed with time and the results are shown in the following Table VIII.

TABLE VIII

| Time (hrs) | Weight Percent of HDDmTU in The Composition | | | | |
|---|---|---|---|---|---|
| | 100% | 70 | 50 | 20 | 0 |
| 0 | white | White with pinkish tint | Very light pink | Very Light pink | Light pink |
| 0.56 | Started turning blue | Pale blue | Very light pink | Very Light pink | Light pink |
| 0.85 | Pale blue | Pale blue | Very light blue | Very Light pink | Light pink |
| 3.16 | Blue | Blue | Pale blue | Light pink | Light pink |
| 8.3 | Dark blue | Dark blue | Blue | Pale violet | Light pink |
| 25.0 | Darker blue | Darker blue | Dark blue | Reddish | Light pink |

As is seen, both the induction period and the rate of color development can be varied by the use of co-crystallized diacetylene monomers.

EXAMPLE 14

Preparation of An Improved Time-Temperature History Indicator

A time-temperature indicator device described schematically in FIG. 1 was constructed.

A piece of filter paper (1.5"×1") was coated with the inactive form of HDDmTU by depositing a solution of HDDmTU in THF onto the paper and allowing to dry. About 0.5"×1" area of the filter paper was left uncoated. A small capillary containing about a drop of liquid p-dioxane was mounted on the uncoated part of the filter paper. The assembly was sealed in a polyester envelope. The indicator was activated at the start of the monitoring process by breaking the glass capillary. The solvent (p-dioxane) was immediately absorbed by the uncoated part of the filter paper, which formed vapor by evaporation. A color change was noted with time which was monitored by comparing formed color with standard Munsell TM color chart. The results in terms of Munsell values are summarized in the following Table IX.

TABLE IX

| Time (days) | Developed Color |
|---|---|
| 0 | White |
| 0.125 | 5PB 9/2 |
| 0.31 | 5PB 8/4 |
| 0.625 | 5PB 8/6 |
| 1.125 | 5PB 8/66 |
| 2.625 | 5PB 7/8 |
| 5 | 5PB 6/8 |
| 10 | 5PB 6/8 |
| 34 | 7.5PB 4/8 |
| 63 | 7.5PB 3/6 |

EXAMPLE 15

A 1"×1" piece of filter paper (Whatman No. 1) coated with the inactive form of HDDmTU was exposed to p-dioxane vapor for 15 minutes. The exposed coated paper was then removed from the source of vapor and sealed in a 2 ml. thick enclosed transparent polyester envelope. Color development occurred and the developing time and shade of developed color noted by comparing with a Munsell color chart. The results were identical with those obtained in Example 14. Thus, the invention process can also be conducted with a device in which the indicator is activated with vapor prior to insertion into the device and subsequent usage.

EXAMPLE 16

The inactive form of HDDmTU was obtained by adding 8 ml. hexane to a solution of 1 g HDDmTU in 12 ml. of acetone at 0° C. The precipitated white crystals were collected and dried at room temperature. They did not undergo color development after standing about a month at room temperature. The X-ray powder diffraction pattern, obtained from a Norelco ® Diffractometer using Copper K alpha radiation, is illustrated as spectrum (c) in FIG. 3.

The above crystals were exposed to p-dioxane vapor overnight and a resulting blue color (red, blue) was observed. The X-ray diffraction pattern, obtained as described above, is illustrated as spectrum (b) in FIG. 3.

HDDmTU was crystallized from p-dioxane, resulting in the active form, and the X-ray pattern is illustrated as spectrum (a) in FIG. 3.

As is seen, in this case the inactive and active forms exhibit strikingly different X-ray crystallographic patterns.

I claim:

1. A composition consisting essentially of at least one member of the group consisting of the inactive forms of 2,4-hexadiyn-1,6-diol bis(m-tolyurethane), 2,4-hexadiyn-1,6-diol bis(o-methoxyphenylurethane), 2,4-hexadiyn-1,6-diol bis(o-chlorophenylurethane), 2,4-hexadiyn-1,6-diol bis-(p-chlorophenylurethane) and co-crystallized compositions thereof, which forms are inactive in the sense that they are unreactive toward polymerization upon thermal annealing by heating below the respective melting points for several hours, and remain colorless after such heating, but which can be transformed into an active form, capable of undergoing solid state polymerization upon thermal annealing, by contacting with vapor consisting essentially of at least one member of the group consisting of p-dioxane, dimethylformamide, and pyridine.

2. A composition consisting essentially of at least one member of the group consisting of the active form of 2,4-hexadiyn-1,6-diol bis(m-tolylurethane), 2,4-hexadiyn-1,6-diol bis(o-methoxyphenyl-urethane), 2,4-hexaxdiyn-1,6-diol bis(o-chlorophenylurethane), and 2,4-hexadiyn-1,6-diol bis(p-chlorophenylurethane), which forms are active in the sense that they are capable of undergoing a color change upon thermal annealing.

* * * * *